United States Patent [19]

Heyneman et al.

[11] 4,242,301
[45] Dec. 30, 1980

[54] AUTOMATED REACTION HOUSING FOR USE IN QUANTITATIVE ANALYSIS

[75] Inventors: Guido Heyneman, Knokke; Christiaan Vandenbossche, Zwijnaarde, both of Belgium; Roland Thieme, Maximiliansau, Fed. Rep. of Germany

[73] Assignee: Siemens Aktiengesellschaft, Berlin & Munich

[21] Appl. No.: 4,370

[22] Filed: Jan. 18, 1979

[30] Foreign Application Priority Data

Feb. 1, 1978 [DE] Fed. Rep. of Germany ....... 2804287

[51] Int. Cl.³ .............................................. G01N 1/10
[52] U.S. Cl. ....................................... 422/68; 422/81; 422/103; 422/104
[58] Field of Search ................... 422/100, 103, 68, 80, 422/81, 104; 73/425.4 R

[56] References Cited

U.S. PATENT DOCUMENTS

| 3,803,004 | 4/1974 | Egri ........................................ 422/68 |
| 4,101,275 | 7/1978 | Taguchi et al. ........................ 422/81 |

FOREIGN PATENT DOCUMENTS 2110742  5/1972  France .

Primary Examiner—R. E. Serwin
Attorney, Agent, or Firm—Hill, Van Santen, Steadman, Chiara & Simpson

[57] ABSTRACT

A temperature-controllable automated reaction housing comprised of a reaction chamber and a jacketed column extending upwards from such chamber and including heat-exchange fluid inlet and outlet lines. The reaction chamber projects at least partially into a controllably heated bath means and includes an outlet nozzle at the bottom of such chamber which is controllable by an automatically controllable valve means for selective removal of contents within such chamber.

3 Claims, 2 Drawing Figures

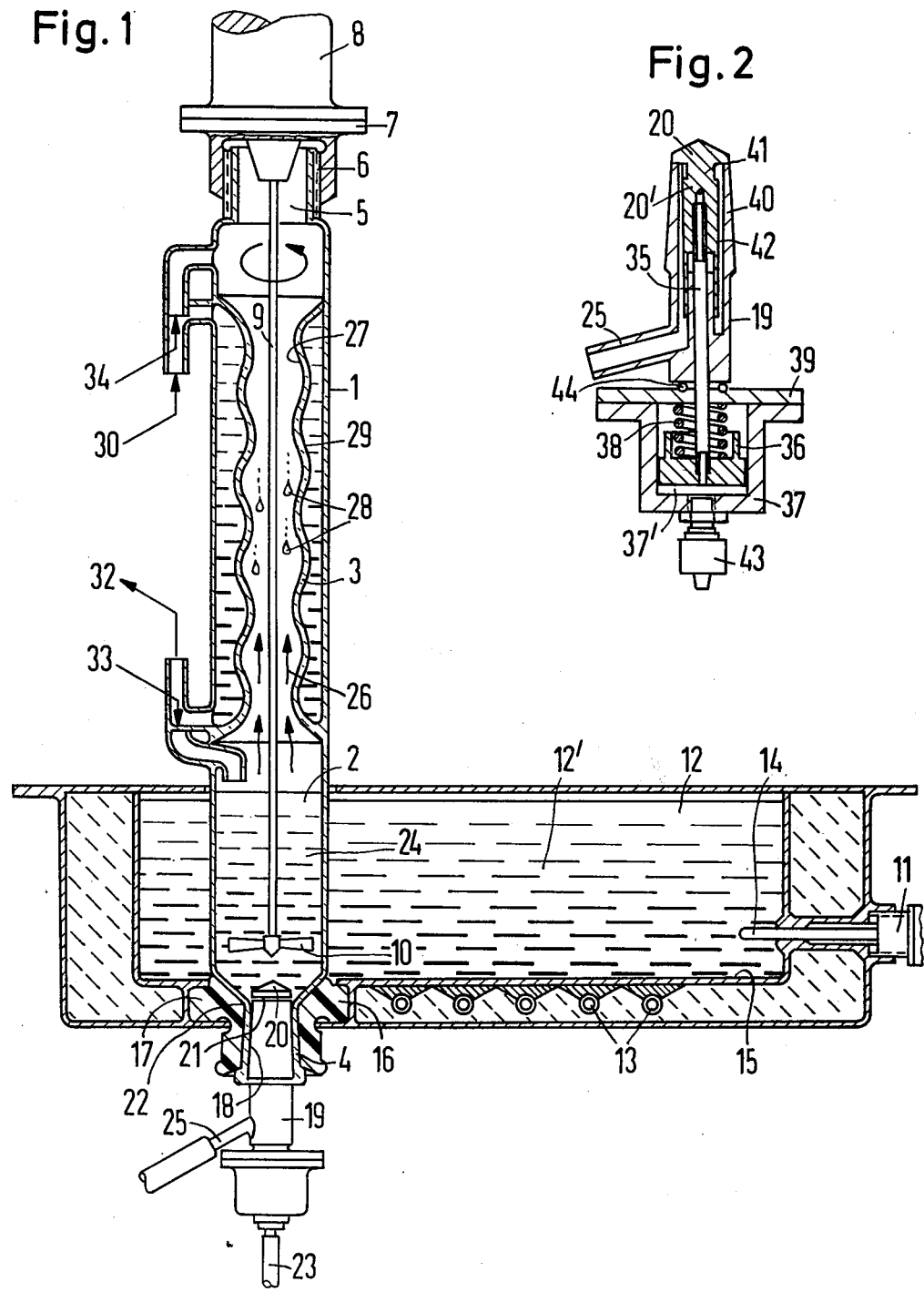

AUTOMATED REACTION HOUSING FOR USE IN QUANTITATIVE ANALYSIS

BACKGROUND OF THE INVENTION

1. Field of the Invention

The invention relates to temperature-controlled reaction containers and somewhat more particularly to a reaction housing useful in a quantitative analysis device wherein organic materials in a water sample are oxidized with a potassium dichromate solution and comprising a temperature-controlled reaction container having inlets, outlets, and agitator means for such oxidation reaction.

2. Prior Art

In determining the amount of water-immiscible solid organic materials in a water source, such as a sewage water source, a defined amount of various reagents, such as sulfuric acid and silver sulfate are admixed with a defined water sample in order to prepare such sample for analysis. Thereafter, the prepared sample is reacted with a $K_2Cr_2O_7$-solution under time-temperature conditions sufficient to oxidize the organic materials in the sample, i.e., by the oxygen released during reduction of $Cr^{+6}$-ions into $Cr^{+3}$-ions. The residual amount of $Cr^{+6}$-ions in the spent reaction mixture is then determined by titrating such mixture with a $Fe^{+2}$-ion containing solution. The consumed amount of $Fe^{+2}$-ion containing solution in such titration provides an indirect indication of the amount of organic material in the water sample under analysis.

In order to carry out the various reaction in this analysis scheme, various embodiments of reaction containers are known in chemical technology. In laboratory procedures, it is conventional to use containers formed of so-called "heat-proof" glass. In order to accomplish the physical and chemical requirements of the foregoing analysis scheme, a system is typically erected comprising of individual sections, which are connected to one another via fluid-flow lines and the like. Typically, the implementation of this analysis scheme occurs in a labroatory set-up and the system for carrying out such scheme is set up on stands on laboratory tables. However, such an arrangement takes up too much space for an analysis device which preferably functions automatically and is not suitable for an analysis automaton.

SUMMARY OF THE INVENTION

The invention provides a reaction housing for use in an analysis automaton.

In accordance with the principles of the invention, a reaction housing or container quantitative analysis is provided which is a space-saving construction and allows a well-governed process to take place therein and allows reaction products or the like to be automatically drained as completely as possible at a time prescribed by a master control means. The reaction housing of the invention comprises an enclosed reaction chamber and a column in communication with the chamber and extending upwardly therefrom. The column is surrounded by a cooling jacket having inlet and outlet nozzles for a heat-exchange fluid. The reaction chamber extends at least partially into a thermastatically controllable bath means and has an outlet nozzle extending from the bottom of such chamber and through the bottom of the bath means. The reaction chamber outlet nozzle is provided with an automatically controllable valve means connected to a master control means.

With a reaction housing constructed in accordance with the principles of the invention, a spacially-confined construction is provided which allows the contents of such housing to be fully removed at any select time. Because the reaction chamber of such a reaction housing is in communication with a reflux condensor, i.e., a coolable column, any vapors arising from a reaction mixture during a reaction thereof within the chamber, can readily condense on the inner surface of the column and constantly flow back into the reaction chamber. The reaction chamber is at least partially surrounded with a heatable bath means, preferably a heatable oil bath, which can be constantly maintained at a select temperature, in the above described analysis scheme, at about 160° C., by a thermostat control means associated with such bath means and coupled to a suitable power source via a master control means. The valve means provided in the bottom of the reaction chamber is preferably actuated with compress gas, whereby, as is known, compressed gas control may be attained via an electromagnetic valve means coupled to a master control means. The reaction chamber as well as the cooling jacket of the reflux condensor are each provided with separate inlet and outlet nozzles. The upper end of the column, away from the reaction chamber, is open and includes a thread sleeve onto which a motor-driven agitator means is provided.

The outlet or drain valve in the bottom of the reaction chamber comprises a hollow conically-shaped spigot which is inserted into a matching conically-shaped outlet opening in the reaction chamber and which includes a tappet means having a sealing cap at the upper end thereof for selectively providing communication between the reaction chamber and the interior of such spigot. The tappet means includes a push rod extending through a cylinder head plate and into contact with a piston within a cylinder. The piston is biased by a centering spring means against the cylinder head plate and is guided during movement thereof by the cylinder walls. A compressed gas inlet nozzle is connected to the opposite or bottom side of the cylinder for actuating the piston. Upon application of a compress gas, the tappet push rod is lifted directly via the piston and the sealing cap opens the mouth of the outlet opening into the reaction chamber. In this manner, any fluids into the reaction chamber can be fully and completely drained.

BRIEF DESCRIPTION OF THE DRAWINGS

Other and further objects of the invention will be apparent from the following description of certain preferred embodiments thereof, taken in conjunction with the accompanying drawing which, by way of illustration, show a preferred embodiment of the present invention and the principles thereof and what is now considered to be the best mode contemplated for applying these principles. Other embodiments of the invention, embodying the same or equivalent principles may be used and structural or other changes may be made as desired by those skilled in the art without departing from the spirit and scope of the novel concepts of the invention, and in which:

FIG. 1 is a partial elevated cross-sectional view illustrating somewhat schematically, an embodiment of reaction housing constructed and operating in accordance with the principles of the invention; and FIG. 2 is similar a partial elevated cross-sectional view, of a valve means utilized in the reaction housing of the invention.

DESCRIPTION OF THE PREFERRED EMBODIMENT

The reaction housing 1 of the invention is useful in quantitative analysis and essentially comprises a reaction chamber 2 having a vertically extending column 3 thereabove, a conically-shaped outlet aperature 4 at the bottom thereof, a threaded open sleeve or neck member 5 on top of the column 3 and a threaded ring member 6 positioned on and attached to the neck member 5. The reaction housing is, preferably, composed of a glass having a high melting point. The threaded ring member 6 includes a flange nut 7 for supporting a motor means 8, which has an output shaft coupled with a rod 9 extending downwardly into the reaction chamber and connected with an agitator 10. The motor means 8 is operationally coupled to a suitable power source, such as electric current source, via a master control means (not shown).

A temperature controllable heating bath means 12 is provided so as to at least partially surround the reaction chamber 2. The bath means 12 is, for example, electrically heated via resistance heating elements 13 provided along a bottom surface 15 thereof. A heat-sensing device 14 extends through a wall of the bath means and in contact with the fluid 12', such as an oil, within the bath means. The heat-sensing device 14 is coupled to a thermostat switch 11, which controls the current supply to elements 13. The switch 11 may be pre-set to maintain any desired temperature within the bath fluid 12' and, when utilized in the earlier described analysis scheme, is set in an exemplary embodiment to maintain a temperature of about 160° C. An aperature 16 is provided along a bottom 15 of the bath means 12 and a ring-shaped sealing member 17 is positioned therein. The outlet aperature 4 of the reaction chamber 2 extends through sealing member 17. In this manner, the sealing member 17 provides support for the reaction chamber and communication is provided between such reaction chamber and other apparatus outside the bath means.

The reaction chamber outlet aperature 4 is conically shaped and includes a conically ground inner surface 18 for supporting and mating with side surfaces of an outlet valve means 19. A valve cap 20 is provided on valve means 19 so that the cap edge 21 is absolutely seated level with the plane containing the mouth 22 of the outlet aperature 4. By upward movement of cap 26, the reaction chamber 2 may be completely drained with such an arrangement.

The valve means 19 is controlled by application of a compressed gas at valve inlet 23. As is explained below, the compressed gas lifts cap 20 upwards so that any fluid 24 in the reaction chamber 2 can drain out through the drain outlet 25 in valve means 19.

Any vapors 26 that may arise during the operation of the reaction housing, travel upwards within column 3 and are condensed on the cooled inner surfaces 27 of such column. Such condensate either flows back into the reaction chamber 2 along the inner column surfaces or drips down, as schematically illustrated at 28. The inner surface of column 23 is cooled by providing a fluid path between inner and outer walls of the column, with a fluid inlet 30 and a fluid outlet 32 interconnecting such fluid path with a source of a heat-exchange fluid, such as water.

The fluids to be reacted (i.e., a water sample and various reagent solutions when the above analysis is being carried out) within chamber 2 are fed thereinto via a fluid inlet nozzle 33. A nozzle 34 at the upper end of the column 3 function as a fluid overflow and a gas outlet passageway and may be connected to a ventilated overflow container (not shown). Nozzle 34 functions to divert fluid into an overflow container when, for example, a blockage occurs at the outlet valve means 19. The inlet nozzle 33 may also be selectively connected to compressed gas source (not shown) for supplying a pressurized gas, such as air, at a pressure of about $5 \cdot 10^{-2}$ bar to the reaction chamber 2. Upon emptying the reaction chamber 2 via valve means 9, a partial vacumm may occur within the reaction chamber and prevent fluid therein from draining. In order to avoid this, when the outlet valve means 19 is opened, a compressed gas is fed via nozzle 33 into the reaction chamber so that substantially all fluids therein flow relatively rapidly through the relatively narrow outlet gap defined between a valve seat 41 and a valve body 40 (best seen at FIG. 2).

Outlet valve means 19, as best seen at FIG. 2, comprises a cap 20 which is connected with a piston 36 via a tappet push rod 35. The piston 36 is mounted in a cylinder 37 which guides it in its up and down movement. A centering spring means 38 is provided within the cylinder and is biased against the cylinder plate 39 and the piston 36, as shown. A valve body 40 is comprised of a hollow shaft conically ground to mate with the inner conical surface of outlet nozzle 4 and the shaft is provided with a ground valve seat 41 at the upper end thereof. Passageways 42 are provided within a guiding portion 20' of cap 20 so that fluid 24 can, upon upward movement of cap 20 from seat 41, flow from the reaction chamber 2 to a drain outlet 25 and from there to other means (not shown). The cylinder 37 is provided with a connecting nozzle 43 for attachment to a compress gas source (not shown). The valve body 40 is sealed from the cylinder plate 39 by a gasket means 44. The cap 20 is firmly urged against seat 41 by the spring means 38. When a compressed gas is fed into a cylinder space 37', it causes the piston 36 to move upwards against the spring and, via the tappet push rod 35 directly connected thereto, to lift the cap 20 from seat 41 so as to open the valve. Upon venting of the compress gas, the valve closes automatically under pressure from the spring means 38.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalence may be resored to, falling within the scope of the invention as claimed.

We claim as our invention:

1. A reaction housing for an automatically operating quantitative analysis device comprising, in combination,
    a reaction chamber having an outlet at a bottom portion thereof and an inlet at a top portion thereof, said outlet including a mouth located at a given plane;
    a hollow column connected to said chamber at said top portion thereof, said column being surrounded by a cooling jacket having a heat-exchange fluid flowing therein;

a thermostatically controllable heating bath means at least partially surrounding said reaction chamber for heating a reaction mixture in said chamber; and an automatically controllable valve means positioned in said outlet of said reaction chamber, said valve means including a cap having sealing edges normally positioned in said given plane to completely seal said outlet mouth, said valve means extending below said bath means for completely draining fluids within said reaction chamber.

2. A reaction housing as defined in claim 1, wherein said reaction chamber outlet is defined by ground conical surfaces and said valve means has ground conical surfaces mating with said outlet conical surfaces.

3. A reaction housing as defined in claim 1, wherein said valve means comprises a hollow conical valve body, a tappet push rod mounted within said valve body, a cap member supported by said push rod, a cylinder having a piston therein spaced from said valve body by a cylinder plate, said push rod being directly connected to said piston and extending through said cylinder plate, said piston being biased away from the cylinder plate by a centering spring means mounted between said plate and said piston.

* * * * *